(12) United States Patent
Hoffman

(10) Patent No.: US 7,516,743 B2
(45) Date of Patent: *Apr. 14, 2009

(54) CONTINUOUS POSITIVE AIRWAY PRESSURE DEVICE AND CONFIGURATION FOR EMPLOYING SAME

(75) Inventor: Leslie Hoffman, Tarzana, CA (US)

(73) Assignee: Viasys Sleep Systems, LLC, Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/787,678

(22) Filed: Apr. 17, 2007

(65) Prior Publication Data

US 2007/0246045 A1 Oct. 25, 2007

Related U.S. Application Data

(60) Provisional application No. 60/793,433, filed on Apr. 20, 2006, provisional application No. 60/793,589, filed on Apr. 20, 2006, provisional application No. 60/793,704, filed on Apr. 20, 2006.

(51) Int. Cl.
*A61M 11/00* (2006.01)
(52) U.S. Cl. .............................. 128/204.23; 128/202.18
(58) Field of Classification Search ............ 128/202.18, 128/202.19, 204.18, 205.18, 205.22, 201.29, 128/202.11, 201.27, 204.22, 204.23
See application file for complete search history.

(56) References Cited

U.S. PATENT DOCUMENTS

| 2,575,483 | A | * | 11/1951 | Bethig | 96/136 |
|---|---|---|---|---|---|
| 4,430,995 | A | * | 2/1984 | Hilton | 128/204.21 |
| 4,494,538 | A | * | 1/1985 | Ansite | 128/205.25 |
| 4,590,951 | A | * | 5/1986 | O'Connor | 128/204.23 |
| 5,042,474 | A | * | 8/1991 | Williamson | 128/206.12 |
| 5,394,870 | A | * | 3/1995 | Johansson | 128/205.22 |
| 5,682,878 | A | * | 11/1997 | Ogden | 128/204.23 |
| 6,834,646 | B2 | * | 12/2004 | Alon et al. | 128/201.22 |
| 7,114,497 | B2 | * | 10/2006 | Aylsworth et al. | 128/204.18 |
| 7,128,069 | B2 | * | 10/2006 | Farrugia et al. | 128/240.18 |
| 7,195,014 | B2 | * | 3/2007 | Hoffman | 128/204.18 |

* cited by examiner

*Primary Examiner*—Steven O Douglas
(74) *Attorney, Agent, or Firm*—Baker & Hostetler LLP

(57) ABSTRACT

A portable continuous positive airway pressure (CPAP) device is adapted for delivering gas under pressure to a patient. The CPAP device comprises a portable housing assembly, a motor blower unit disposable within the portable housing assembly, a user interface configured to be engaged to the patient, and a patient hose extending between the user interface and the motor blower unit. The portable housing assembly may be comprised or configured as a wearable frontpack assembly which is configured to be worn against the patient's chest. The frontpack assembly may include a pair of shoulder straps configured to extend over the patient's shoulders and under the patient's arms to secure the CPAP device to the patient. The motor blower unit may be remotely disposed from the portable housing assembly such as on a bedside assembly or on a tabletop stand.

18 Claims, 6 Drawing Sheets

CONTINUOUS POSITIVE AIRWAY PRESSURE DEVICE AND CONFIGURATION FOR EMPLOYING SAME

CROSS-REFERENCE TO RELATED APPLICATIONS

The present application claims priority to U.S. Provisional Application Nos. 60/793,433 and 60/793,589 and 60/793,704, each filed on Apr. 20, 2006, the entire contents of each being expressly incorporated by reference herein. The present application is also related to commonly-owned U.S. Pat. No. 7,195,014 entitled PORTABLE CONTINUOUS POSITIVE AIRWAY PRESSURE SYSTEM filed on May 13, 2005, and to U.S. patent application Ser. No. 11/649,674 entitled USER INTERFACE AND HEAD GEAR FOR A CONTINUOUS POSITIVE AIRWAY PRESSURE DEVICE filed on Jan. 4, 2007, the entire contents of each being incorporated by reference herein.

STATEMENT RE: FEDERALLY SPONSORED RESEARCH/DEVELOPMENT (Not Applicable)

BACKGROUND

The present invention relates generally to patient ventilation systems and, more particularly, to a uniquely-configured portable continuous positive airway pressure (CPAP) device that may be worn by a patient and which is specifically adapted to provide enhanced patient mobility and comfort as a means to improve patient compliance with prescribed CPAP therapy.

Obstructive sleep apnea (OSA) is a serious breathing disorder affecting as many as one in five adults and is a characterized by a temporary collapse of the throat resulting in a pause in breathing during sleep. Each OSA episode can occur hundreds of times in a single night with each occurrence disrupting the patient's sleep or awakening the patient. Left untreated, OSA can lead to severe and even life-threatening consequences.

The link between OSA and hypertension, stroke and heart failure is well-documented. Serious cases of OSA can result in sleep deprivation or insomnia which, over time, can result in moodiness, irritability, memory loss, poor judgment and an overall poor quality of life. Even further, patients suffering from OSA have a dramatically increased risk of traffic accidents and an increased mortality rate due to medical complications stemming from this disorder.

In severe cases of OSA, doctors prescribe CPAP therapy wherein a constant flow of positively pressurized gas is supplied to the patient during sleep. The gas is typically pressurized to between 5 and 20 cm $H_2O$ and is delivered to the patient's airway in order to hold the throat open and allow for uninterrupted breathing during sleep. Conventional CPAP devices typically include a blower unit connected by a patient hose to a mask. The mask acts as a nasal or oral interface and introduces pressurized gas into the patient's throat. The blower unit of conventional CPAP devices is typically powered by an electric motor which, due to noise, vibration and heat produced during its operation, must be mounted on a table or a stand located adjacent the patient's bed to avoid disrupting the patient's sleep.

Conventional CPAP patient hoses are flexible tubes typically provided in a standard six-foot length. The patient hose extends between the bedside blower unit and the mask which is mounted on the patient's head. Because of its long length and because the patient hose extends laterally or sideways from the patient to the blower unit, a sideways "torqueing" or pulling force is imposed by the patient hose on the mask. The torqueing or pulling by the patient hose results in poor sealing of the mask against the patient's face. In addition, the sideways pulling on the mask may also create pressure points against the patient's face and results in general patient discomfort.

For patients who use nasal prongs, the sideways tugging can cause irritation of the patient's nose due to the close-fitting engagement of the prongs with tender mucous tissue lining the patient's nostrils. For patients who use a nasal mask which seals around an exterior of the patient's nose, the tugging of the patient hose can prevent proper sealing of the mask and can also cause eye irritation as a result of pressurized gas leaking around the nose bridge of the mask and flowing into the patient eyes.

Another problem associated with the lengthy patient hose of conventional CPAP devices is the occurrence of condensation in the patient hose. Some conventional motor blower units operate at a relatively high temperature such that the pressurized gas produced thereby is typically heated. As the heated gas travels along the lengthy hose from the blower unit to the patient, the gas cools because the temperature of ambient air in the room is typically lower than the temperature of the pressurized gas. Moisture in the pressurized gas therefore condenses within the hose interior. During a period of use, this condensation can result in water buildup and the patient hose then becomes a breeding ground for bacteria resulting in colds and other health complications for the patient.

Closely related to the problem of tugging by the patient hose is a general lack of mobility associated with conventional CPAP devices. For patients who get up many times during the night, the patient hose acts as a restraint on movement as the patient is effectively tethered to the bedside blower unit. For those with active sleep patterns, the lengthy patient hose inhibits normal body shifting movements and turning from side-to-side to which the patient is accustomed such that the hose makes falling asleep difficult or prevents sleep altogether.

The above-mentioned problems associated with the patient hose are responsible in large measure for the generally low rate of compliance by patients who have started CPAP therapy. Other factors responsible for the low compliance rate include a general dislike of the medical-equipment appearance of a bedside CPAP device in a bedroom environment. Many patients simply have a general aversion to conventional CPAP devices.

As can be seen, there exists a need in the art for a portable CPAP device that provides greater freedom of movement than conventional bedside CPAP devices. More particularly, there exists a need in the art for a wearable CPAP device that provides increased patient mobility but without the problem of the patient hose tugging on the mask as is commonly associated with conventional bedside CPAP devices. In addition, there exists a need in the art for a portable CPAP device that may be constructed in a wide range of configurations that may be conveniently operated in close proximity to the patient without disturbing the patient's sleep.

BRIEF SUMMARY

The present invention specifically addresses and alleviates the above referenced deficiencies associated with conventional CPAP devices and other ventilation systems of the prior art. In one embodiment, the present invention comprises a portable CPAP device comprising a portable housing assembly configured in a variety of assemblies including a vest assembly, a frontpack assembly, a backpack assembly, a pillow assembly, a bedroll assembly and in the shape of plush toy such as a stuffed animal. Contained within the portable housing assembly is a motor blower unit which is configured to produce pressurized gas. The CPAP device further includes a user interface such as nasal mask or pair of nasal prongs which are engageable to the patient's face. A patient hose extends between the user interface and the motor blower unit located within the portable housing assembly for delivering the pressurized gas to the user interface.

The self contained CPAP device integrates the motor blower unit into the portable housing assembly in any one of the above-mentioned configurations of the portable assembly. The vest assembly arrangement of the CPAP device is similar to that which is described in greater detail in U.S. Pat. No. 7,195,014 filed on May 13, 2005, the entire contents of which is expressly incorporated by reference herein. The vest assembly comprises first and second side panels interconnected by a collar portion of reduced cross sectional area relative to the cross sectional area of each of the panels. The motor blower unit is installed in one of the panels while a control unit and a power source such as a battery pack are located in the opposing panel in order to achieve a weight-balanced arrangement.

In a further embodiment, the portable housing assembly may be configured as a frontpack assembly configured to be worn against the patient's chest and which is securable such as by means of a system of straps, clips, or other fastener means. For example, the frontpack assembly may include a pair of shoulder straps disposed on opposing sides of the frontpack assembly. The shoulder straps preferably extend from the upper edge thereof over the patient's shoulders and under the patient's arms and connecting to a lower edge or side edge of the frontpack assembly. A cross strap may be provided on the patient's back in order to interconnect the shoulder straps to better secure the frontpack assembly to the patient. The frontpack assembly is adapted to contain the motor blower unit, control unit and power source (i.e., battery pack) in a uniformly distributed manner.

In a further embodiment, the motor blower unit may be disposed remotely from the portable housing assembly. More specifically, the motor blower unit may be housed in a bedside housing or tabletop housing. An extension hose fluidly connects the motor blower unit to the portable housing assembly worn by the patient. A patient hose extends from the portable housing assembly to a nasal mask or nasal prongs or other user interface. The portable housing assembly may include a conduit which fluidly connects the patient hose to the extension hose.

In further alternative configurations, the portable housing assembly may be configured as a backpack assembly also having a pair of shoulder straps disposed on opposing sides thereof. The backpack assembly may include an optional waist strap for securing around the patient's waist. The portable housing assembly may also comprise the pillow assembly or the bedroll assembly which are configured to be positioned adjacent the patient such as near the patient's head when the patient is sleeping. The pillow assembly and bedroll assembly include the above-mentioned operative components (e.g., motor blower unit, power source, control unit).

In each of the above-described configurations, resilient material forms the shape and contour of the portable housing assembly. The resilient material may be a foam material which includes a plurality of cavities for containing the various components which are electrically connected to one another such as via conductive wiring. The foam is preferably a memory foam material. For the pillow assembly and bedroll assembly, the foam may be formed as two separate halves or sections which are insertable into an outer cover of soft material.

The liner may include an opening through which the halves or sections may be inserted. Ideally, the portable housing assembly are sized and configured such that the resilient material provides sufficient padding such that the patient may use any of the above-mentioned configurations as a pillow or for support when sleeping. Due to the minimal amounts of vibration, noise and heat generated by the motor blower unit as well as due to the compact size of the portable housing assembly, the CPAP device may be conveniently and comfortably used by the patient to provide respiratoy therapy without disturbing the patient's sleep.

BRIEF DESCRIPTION OF THE DRAWINGS

These and other features of the present invention will become more apparent upon reference to the drawings wherein like numbers refer to like parts throughout and wherein.

DETAILED DESCRIPTION

Figure 1:
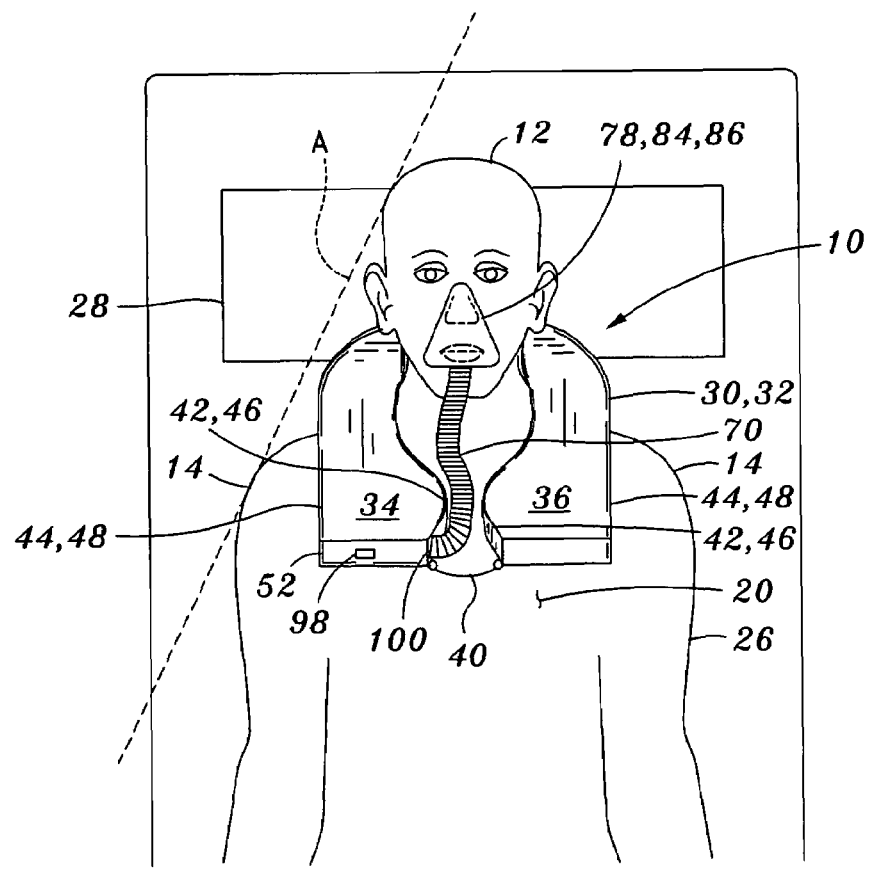
FIG. 1 is a top view of a patient wearing a portable continuous positive airway pressure (CPAP) device comprising a portable housing assembly configured as a vest assembly.

Referring now to the drawings wherein the showings are for purposes of illustrating preferred embodiments of the present invention and not for purposes of limiting the same, shown is a portable continuous positive airway pressure (CPAP) device 10 adapted for delivering gas under pressure to a patient 12. In its broadest sense, the CPAP device 10 comprises a portable housing assembly 30, a motor blower unit 108, a user interface 78, and a patient hose 70 extending between the user interface 78 and the motor blower unit 108. In one embodiment, the portable housing assembly 30 is specifically adapted to be worn by or attached to the patient 12 in order to avoid the problem of prior art CPAP devices in which the patient hose 70 tugs against the patient mask.

More particularly, such prior art CPAP devices typically include a bedside blower unit connected by a lengthy patient hose to a nasal mask 86 or nasal prongs 88 (i.e., user interface 78) mounted on the patient's face. The sideways torque or pulling force exerted by the lengthy patient hose of conventional CPAP devices leads to poor sealing of the user interface 78 on the patient's face and may also create pressure points against the patient's face resulting in general patient discomfort. Advantageously, the portable housing assembly 30 of the present invention employs a shorter length and centrally-located patient hose 70 extending downwardly from the user interface 78 to the portable housing assembly 30 mounted directly on the patient 12 in one of several embodiment illustrated in the figures to reduce the above-mentioned tugging problem and to provide greater freedom of movement to the patient.

Referring particularly now to FIGS. 1-6, shown is the patient 12 wearing the portable housing assembly 30 which is ergonomically-designed in a self-contained vest assembly 32. In one configuration illustrated in FIG. 5, the motor blower unit 108 may be disposed remotely from the vest assembly 32 and may be fluidly connected thereto such as by the extension hose 106. In either embodiment, the motor blower unit 108 is operable to produce pressurized gas which is delivered to the patient 12 via the patient hose 70 at the user interface 78 which is mounted on the patient's head.

Figure 6:
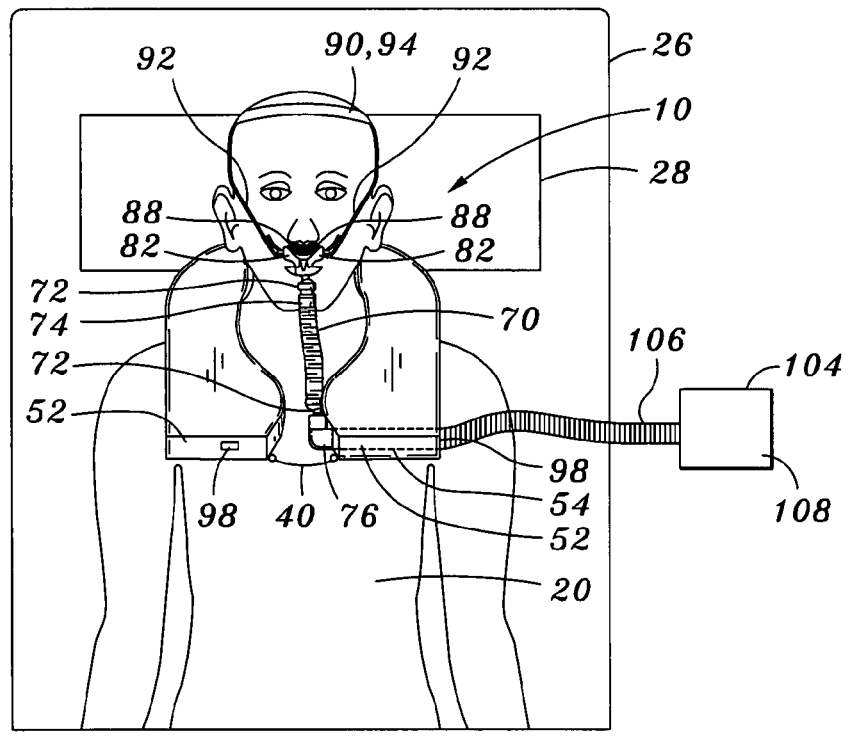
FIG. 6 is a top view of the vest assembly disposed around the patient's neck and further illustrating a user interface configured as a pair of nasal prongs secured to the patient's head by means of head gear.

The user interface 78 may be provided in kit form and may generally comprise a manifold member 80 and a gas delivery member 84. The gas delivery member 84 is provideable in a variety of alternative configurations such as the nasal mask 86 illustrated in FIGS. 1-2 and 6-10 or as a pair of nasal prongs 88 illustrated in FIG. 6. The manifold member 80 may allow for interchangeability of the nasal mask 86 with the nasal prongs 88 without disconnecting the patient hose 70. As can be seen in FIG. 6, the patient hose 70 may optionally include a pair of ball joints 72 at opposing ends of the patient hose 70. If included, the ball joints 72 increase flexibility in patient movement, improve patient comfort and improve overall efficacy of CPAP therapy due to reduced leakage at the nasal mask 86 or nasal prongs 88.

The user interface 78 may be secured to the patient's face by various mechanisms. For example, in FIG. 6, head gear 90 comprising a head strap 94 and a pair of side straps 92 secured to strap rings 82 stabilize the nasal prongs 88 to the patient's face using adjustable fasteners (e.g., Velcro) to fit a variety of head sizes. Likewise, the nasal mask 86 illustrated in FIGS. 1-2, 5 and 7-10 may be secured to patient's head by means of the head gear 90. Alternatively, the head gear 90 may be altogether omitted in certain embodiments due to a biasing force applied to the user interface 78 as a result of the orientation of the patient hose 70 which the forces the nasal mask 86 into sealing engagement with the patient's face.

Figure 2:
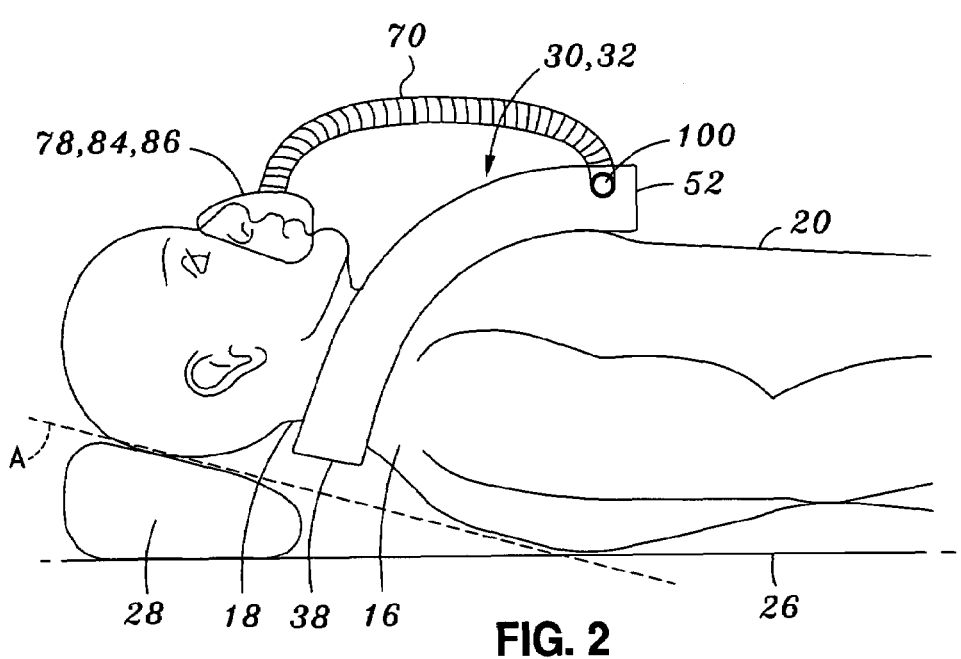
FIG. 2 is a side view of the patient wearing the vest assembly.

Referring still to FIGS. 1-6, the vest assembly 32 may comprise a first panel 34 and a second panel 36 interconnected by a collar portion 38 as described in greater detail in U.S. Pat. No. 7,195,014 entitled Portable Continuous Positive Airway Pressure System, the entire contents of which is incorporated by reference herein. As can be seen, the collar portion 38 has a reduced cross sectional area relative to the cross sectional area of the panels 34, 36 such that the collar portion 38 fits within a nape 18 of the patient's neck 16 as best seen in FIG. 2. The motor blower unit 108 is housed in one of the first and second panels 34, 36. A control unit 130 and battery pack for the motor blower unit 108 is housed in the remaining one of the panels 34, 36.

Each of the first and second panels 34, 36 includes an inner surface which rests against the patient's chest 20. Housed within the second panel, the control unit 130 contains control buttons and a display screen (not shown) for regulating operation of the CPAP device 10. The control unit 130 is oriented on an exterior side of the panel and is therefore exposed to enable observation of the display and to allow manipulation of the control buttons.

Referring to FIG. 1, the first panel 34 preferably includes an air inlet 98 located adjacent the lower edge 52 of the first panel 34 near the motor blower unit 108 to serve as an air intake. An air outlet 100 is likewise disposed adjacent a lower side or edge 52 of the first panel 34 but preferably opens toward an inner side 42 or inner edge 46 of the first panel 34 in order to facilitate connection to the centrally-located patient hose 70 which extends downwardly from the patient's head. The first and second panels 34, 36 may be interconnected to one another by means of a panel tie 40 which, optionally, may include electrically conductive wiring 134 to connect the power source 132 to the motor blower unit 108. Additionally, the panel tie 40 serves to stabilize the vest assembly 32 on the patient's chest 20 by maintaining the orientation and relative position thereof. In this regard, the panel tie 40 may be mechanically fastened to the patient clothing to further stabilize the vest assembly 32 against movement.

Referring briefly to FIG. 2, the reduced cross sectional area of the collar portion 38 is apparent wherein the collar portion 38 fits within the nape 18 area of the patient's neck 16. The collar portion 38 is sized to lie within a clearance plane indicated by the reference character A. The clearance plane A extends from the patient's head (shown in FIG. 2 resting on a head pillow 28) to the shoulder blades of the patient 12. In this manner, interference between the collar portion 38 and the patient's head pillow 28 or bed 26 is minimized and therefore maximizes freedom of movement.

Furthermore, the vest assembly 32 is configured such that the first and second panels 34, 36 and the collar portion 38 lie within the clearance plane identified by the reference character A in FIG. 1 wherein the patient 12 is viewed from the front. In FIG. 1, the clearance plane A extends from a side of the patient's head to the sides of the patient's shoulders 14. By configuring the vest assembly 32 to fit within the clearance planes A illustrated in FIGS. 1 and 2, patient comfort and mobility are maximized which is particularly advantageous for those with active sleep patterns.

Referring to FIGS. 1 and 2, the patient hose 70 extends between the user interface 78 and the motor blower unit 108 contained within the first panel 34 of the vest assembly 32. The patient hose 70 is preferably flexible in nature and, in this regard, may be fabricated of polymeric material such as silicone rubber. The patient hose 70 may be formed of conventional CPAP tubing of a standard diameter. Such tubing material preferably has a smooth inner bore in order to eliminate air flow restrictions on the pressurized gas passing therethrough and to minimize noise produced by pressurized gas.

Referring briefly to FIG. 6, the patient hose 70 may include a pair of ball joints 72 disposed at opposed ends of the patient hose 70. The ball joints 72 may be configured to be removably connectable to the opposing hose ends in order to allow greater patient mobility than would be otherwise achievable with a fixed connection at the user interface 78 and air outlet 100. A connector elbow 76 may also be provided at the lower end of the patient hose 70 and the motor blower unit 108 in order to minimize lateral forces. The connector elbow 76 forms a right-angle turn from the air outlet 100 and may further provide a swivel capability to the patient hose 70.

Figure 3:
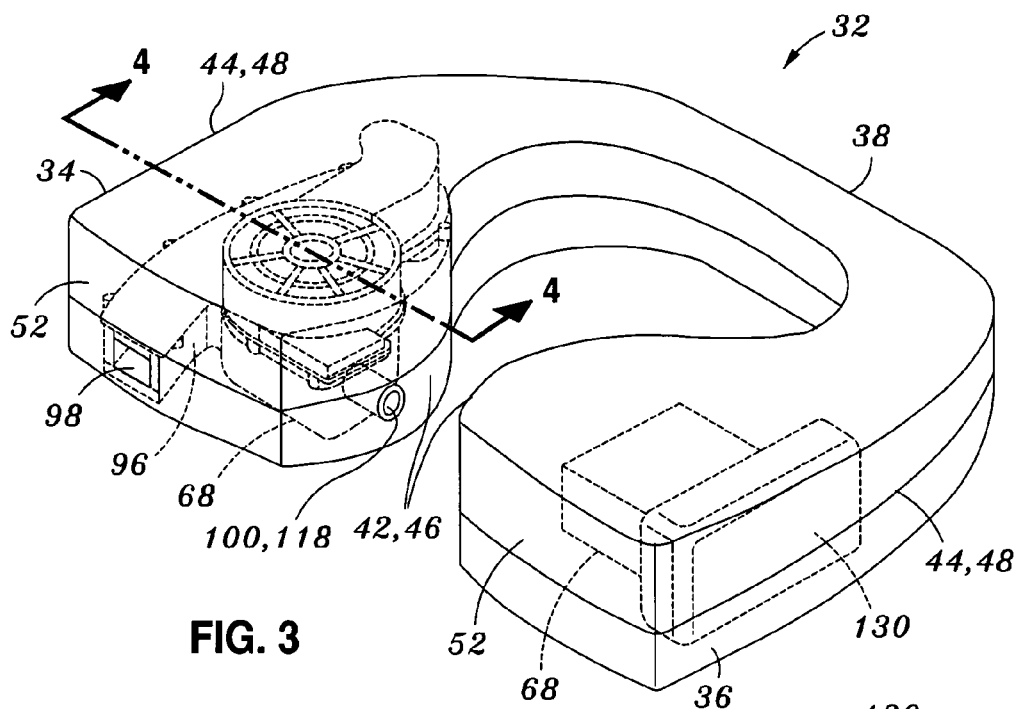
FIG. 3 is a perspective view of the vest assembly comprising first and second panels and having the motor blower unit incorporated into the first panel and a power source/battery pack incorporated into the second panel.
Figure 4:
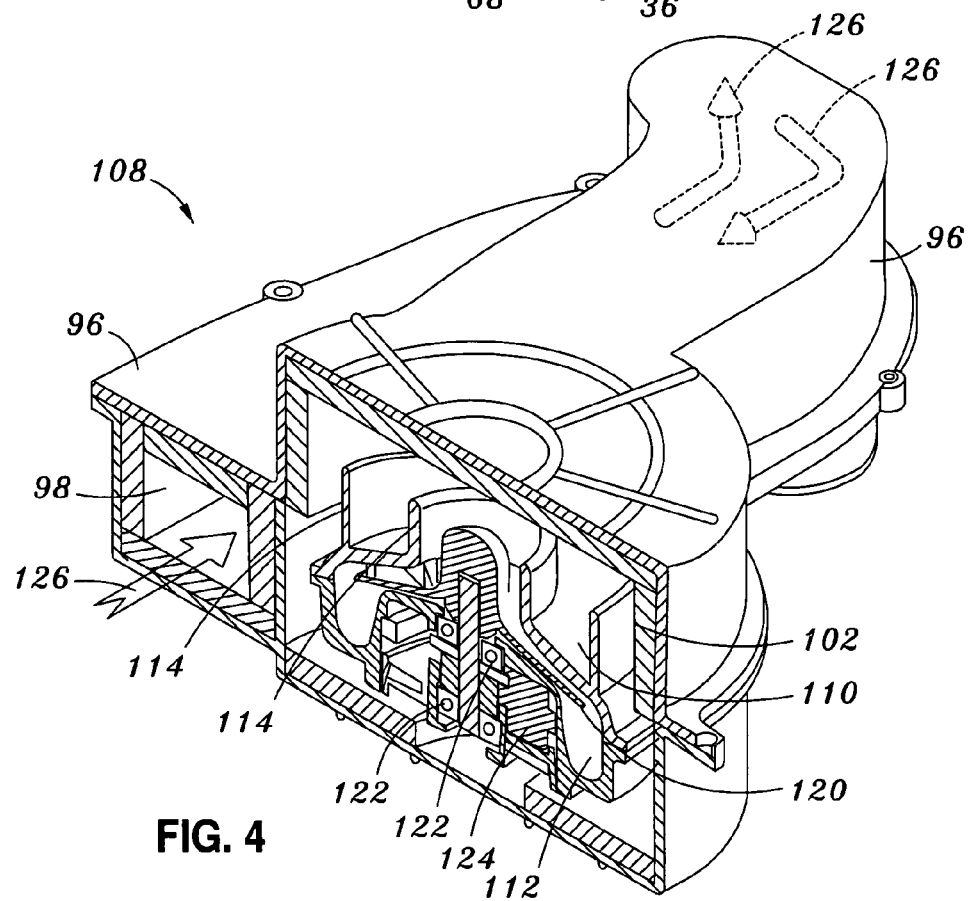
FIG. 4 is a perspective cut-away view of the motor blower unit illustrating a blower assembly disposed within a blower chamber.

Referring to FIGS. 3 and 4, shown is the motor blower unit 108 disposed within the first panel 34 and the control unit 130 being disposed within the second panel 36. As was earlier mentioned, the power source 132 (i.e., battery pack) may be contained within the second panel 36. The air inlet 98 is preferably located at the lower edge 52 of the first panel 34 near the motor blower unit 108 to serve as an air intake. The air outlet 100 is likewise disposed adjacent the lower edge 52 but preferably opens toward the inner side 42 of the first panel 34 to facilitate connection to the patient hose 70.

As shown in FIG. 4, the motor blower unit 108 is mounted within a blower chamber 102 of a device housing 96 of the CPAP device 10. The motor blower unit 108 comprises a blower housing 110 which defines an interior annular housing or volute 112 and houses a motor assembly 124 which is operative to rotate an impeller 120 adapted to compress air that is drawn into an annular blower inlet 116. Due to the optimized geometry of the impeller 120 and volute 112, the motor blower unit 108 is effective in minimizing aerodynamic losses and excessive noise generated during compression of the air. The motor blower unit 108 efficiently generates the desired pressurized gas flow required for CPAP therapy with minimal power consumption by the motor assembly 124.

In one embodiment, the motor assembly 124 is preferably powered by a brushless D.C. motor assembly 124 comprising a stator assembly and a rotor magnet that is rotatable about the stator assembly. A bearing 122 assembly is preferably integrally molded into the stator assembly and rotatably couples the rotor magnet to the stator assembly. The motor assembly 124 may be configured as a three-slot/two-pole brushless D.C. motor assembly 124 wherein the stator assembly comprises three core sections and the rotor magnet comprises two opposing poles. The core sections are sequentially magnetizable during rotation of the rotor magnet due to the sequential application of current from the power source 132 (e.g., battery pack).

To minimize the transmission of vibration from the blower assembly to the vest assembly 32, the motor blower unit 108 may be mounted on a set of foam pads or rubber standoffs (not shown) to mechanically isolate the blower housing 110 from the device housing 96. Additionally, the bearing 122 assembly upon which the motor shaft and impeller 120 are rotatably supported are preferably precision bearings 122 and are mounted in an arrangement that minimizes lateral movement of the impeller 120 relative to the housing interior chamber or volute 112.

The motor blower unit 108 is also configured to minimize the generation of excessive levels of vibration and/or noise as may otherwise occur over time due to normal wear-and-tear in the bearings 122. Noise is further suppressed by optionally including a pair of first and second annular baffles 114 on the upper portion of the blower housing 110 as best seen in FIG. 4. The annular baffles 114 suppress the radiation of mechanical noise produced by the rotating impeller 120/bearing 122 assembly. Furthermore, the annular baffles 114 help to attenuate noise that is generated by movement of air through the blower chamber 102.

Referring still to FIG. 4, the device housing 96 is constructed in a clam-shell arrangement having an outer cover which is secured to a lower frame of the device housing 96. Air movement noise generated within the device housing 96 is attenuated by configuring the device housing 96 such that the air flow path 126 includes several directional changes indicated by the dashed arrows in FIG. 4. In this regard, the device housing 96 defines two ducts having different lengths in order to attenuate different frequency bands.

The ducts are oriented to prevent line-of-sight from the air inlet 98 to the blower inlet 116. Each of the ducts is preferably lined with dissipative elements such as open cell foam in order to absorb acoustic energy generated by air movement. The combination of the lined device housing 96 with the complex flow path 126 and the annular baffles 114 of the blower housing 110 collectively reduce noise generated by air movement through the device housing 96 and mechanical noise generated by the motor assembly 124.

Referring briefly back 22 to FIG. 3, the power source 132 (i.e., battery pack) is preferably disposed with the second panel 36. The control unit 130 may also be disposed within the second panel 36 and is electronically coupled to the power source 132 and to the motor blower unit 108 such as via the panel tie 40 illustrated in FIG. 1. Preferably, the battery pack is a highly efficient battery such as a lithium ion battery to maximize operating time of the motor blower unit 108 between recharges or battery replacement. The control unit 130 may include a charging receptacle or a jack in order to permit recharging of the battery pack. The high operating efficiency of the motor blower unit 108 enables operation of the CPAP device 10 for extended periods of time with minimal heat buildup in the vest assembly 32.

As illustrated in FIG. 3, the power source 132 and control unit 130 are housed in one of the panels 34, 36 while the motor blower unit 108 is preferably housed in an opposite one of the panels 34, 36 to equalize weight distribution within the vest assembly 32. The equally distributed weight stabilizes the vest assembly 32 against movement on the patient's chest 20. However, it should be noted that the motor blower unit 108, control unit 130 and power source 132 may be positioned within the vest assembly 32 in any configuration. Positioning the motor blower unit 108 toward the lower edge 52 of the panel is believed to be most preferable in that any noise, heat or vibration generated by the motor blower unit 108 is placed as far from the patient's face as possible.

The air inlet 98 for the motor blower unit 108 is preferably located along the lower edge 52 of one of the panels 34, 36 such that air movement noise or mechanical noise of the motor assembly 124 is directed away from the patient 12. Furthermore, locating the air inlet 98 on the lower edge 52 of the panel minimizes the risk of blockage thereof such as by the patient's head pillow 28, blankets or patient's sleepwear. However, the air inlet 98 may be located in a variety of alternative locations such as on the upper edge 50 or side edges of the portable housing assembly 30 as may be desirable for certain embodiments such as those illustrated in FIGS. 7-12, as will be described in greater detail below.

Likewise, the air outlet 100 is preferably located adjacent the center of the patient's torso such that the patient hose 70 extends upwardly to the user interface 78 as illustrated in FIGS. 1, 5-6, 8 and 10. As was earlier mentioned, the advantages provided by the vertically-centered patient hose 70 include elimination of the sideways tugging forces exerted by laterally extending patient hoses of conventional bedside CPAP devices 10. In addition, due to its short length, the patient hose 70 has less mass or weight than conventional CPAP hoses and therefore minimizes downward force exerted on the user interface 78.

Figure 5:
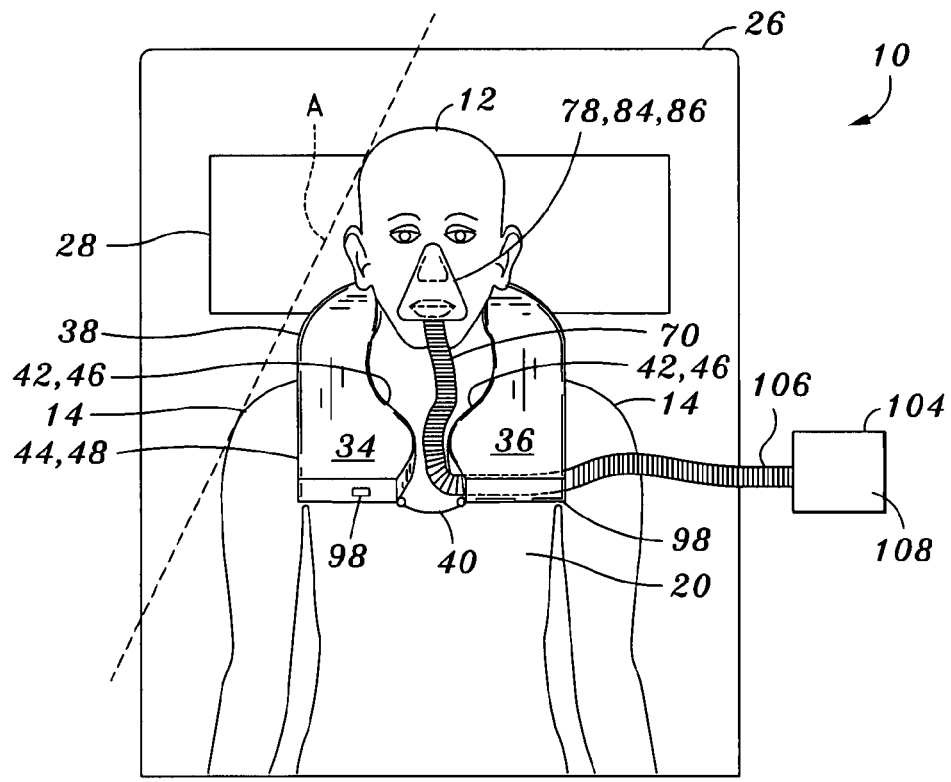
FIG. 5 is a top view of the patient wearing the vest assembly in an alternative embodiment wherein the motor blower unit is remotely disposed from the vest assembly and is fluidly connect thereto by an extension hose.

Referring to FIG. 5, shown is the CPAP device 10 in an embodiment wherein the motor blower unit 108 is disposed remotely from the vest assembly 32. More specifically, the motor blower unit 108 may be mounted on a bedside stand such as in a tabletop housing 104. The CPAP device 10 includes an extension hose 106 which is extendable between the motor blower unit 108 and the vest assembly 32 for delivering pressurized gas to the vest assembly 32. The vest assembly 32 includes a tubing member or conduit 54 extending along the lower edge 52 of one of the panels 34, 36.

The conduit 54 is preferably, but optionally, contained within the lower edge 52 of one of the panels 34, 36 and fluidly connects the patient hose 70 to the extension hose 106. The wearable vest assembly 32 illustrated in FIG. 5 anchors the patient hose 70 to the patient's chest 20 such that the vest assembly 32 decouples lateral forces otherwise imposed by conventional CPAP devices 10. Because of its securement to the patient's torso, lateral tugging forces induced by the extension hose 106 are largely borne and dispersed by the vest assembly 32.

The extension hose 106 is preferably fabricated of conventional CPAP tubing as described above with regard to the patient hose 70. Furthermore, the extension hose 106 is preferably configured to be easily disconnected from the vest assembly 32 to facilitate drying of the interior of the patient hose 70 as is recommend following each period of use. Likewise, in each of the configurations of the portable housing assembly 30 described herein, the patient hose 70 and extension hose 106 are each preferably configured to allow compete removal thereof to facilitate drying after each use which may minimize the formation of mold or bacteria.

It should also be noted that the vest assembly 32 illustrated in FIG. 5 may be provided in an arrangement wherein the motor blower unit 108 is contained within the first panel 34 and may also include the section of conduit 54 disposed within the second panel 36. Such an arrangement allows the patient 12 to receive CPAP therapy in the self-contained version (FIG. 1) until loss of battery power at which time the patient 12 may switch to the tabletop version (FIG. 5) to resume CPAP treatment.

Referring now to FIGS. 7-10, shown is the portable housing assembly 30 comprised of a wearable frontpack assembly 56 which is specifically configured to be worn against the patient's chest 20. In one embodiment, the frontpack assembly 56 is adapted to house the motor blower unit 108. The frontpack assembly 56 is stabilized against the chest 20 of the patient 12 by a pair of shoulder straps 58 disposed on opposing sides of the frontpack assembly 56. As can be seen, each one of the shoulder straps 58 extends from an upper portion or upper edge 50 of the frontpack assembly 56 and is configured to extend over the patient's shoulders 14 and under the patient's arms 24 and reattaching to an outer side 44 or edge 48 or lower edge 52 of the frontpack assembly 56. However, it should be noted that the frontpack assembly 56 may include only a single strap or a plurality of straps disposed in varying configurations suitable for stabilizing the frontpack assembly 56 on the patient's torso.

Figure 7:
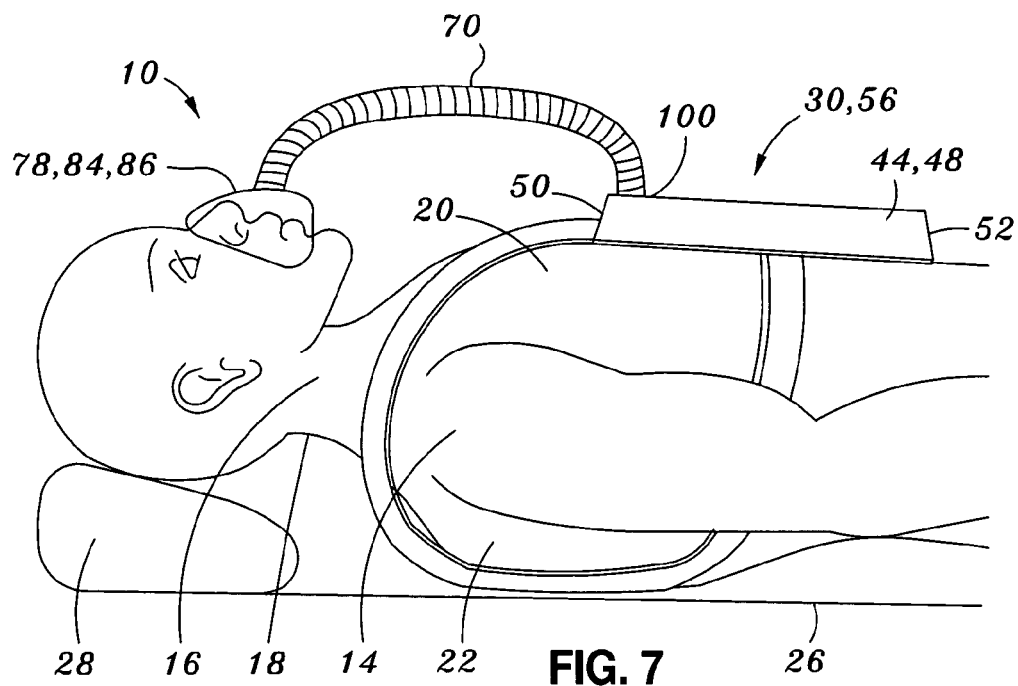
FIG. 7 is a side view of the patient wearing the portable housing assembly configured as a frontpack assembly configured to be worn against the patient's chest.

FIG. 7 illustrates the frontpack assembly 56 worn by the patient 12 resting on a bed 26 in a supine position with the head pillow 28 supporting the patient's head. As can be seen, the patient hose 70 extends from an upper edge 50 or upper portion of the frontpack assembly 56 to the user interface 78. In one embodiment, the patient hose 70 extends laterally outwardly or upwardly from the frontpack assembly 56 and interconnects to the user interface 78 (i.e., nasal mask 86, nasal prongs 88) in such a manner as to provide a biasing force against the user interface 78. In this arrangement, the patient hose 70 stabilizes the nasal mask 86 against the patient's face to eliminate the need for head gear 90 which may be a source of discomfort in certain patients. However, for configurations where the user interface 78 is configured as a pair of nasal prongs 88 as shown in FIG. 6, head gear 90 may be required and may be utilized in the manner illustrated.

The frontpack assembly 56 provides a self contained portable, wearable CPAP device 10 for treatment of obstructive sleep apnea (OSA) and other respiratory disorders in the same manner as was described above with reference to the vest assembly 32. In this regard, the frontpack assembly 56 provides the same attributes as the vest assembly 32 in decoupling lateral tugging forces exerted on the user interface 78 by conventional CPAP hoses that extend to a bedside motor blower unit. The frontpack assembly 56 may have a generally rectangular shape although other shapes are contemplated. The frontpack assembly 56 contains the motor blower unit 108, the power source 132 such as a battery pack, and the control unit 130 by which operation of the CPAP device 10 may be regulated. The motor blower unit 108 is preferably located at a lower portion or lower edge 52 of the frontpack assembly 56 in order to maximize its distance from the patient's face. In this regard, any noise, heat or vibration generated during operation of the motor blower unit 108 is positioned away from the patient's face to minimize disruption of sleep.

Figure 8:
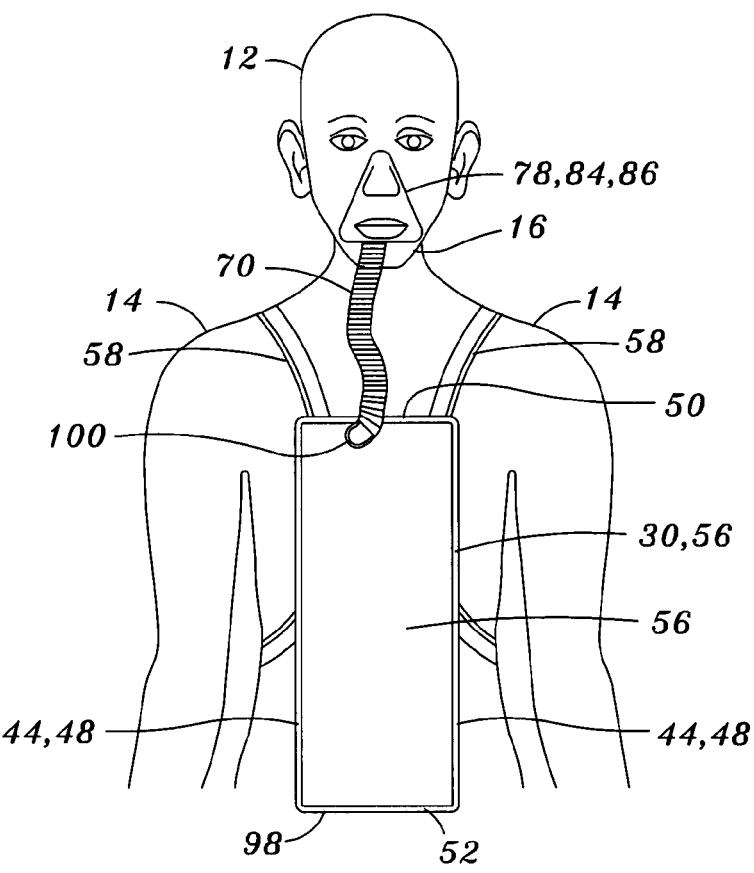
FIG. 8 is a top view of the frontpack assembly containing the motor blower unit and being fluidly connected to the user interface by means of a patient hose.

As shown in FIG. 8, the frontpack assembly 56 has inner, outer, upper and lower edges 46, 48, 50, 52 which are preferably sized to fall within the chest area of the patient 12. The air inlet 98 to the motor blower unit 108 is preferably located along the lower edge 52 of the frontpack assembly 56 similar to that which is illustrated in FIGS. 1 and 5. The conduit 54 may be embedded within the frontpack assembly 56 and extends from the blower outlet 118 to the lower end of the patient hose 70 located at the upper edge 50 of the frontpack assembly 56. The patient hose 70 extends up to the user interface 78 which may be configured in a variety of configurations including a nasal mask 86 shown in FIGS. 7-10 and the nasal prongs 88 illustrated in FIG. 6. However, any variety of user interface 78 configurations may be used with the frontpack assembly 56.

Figure 9:
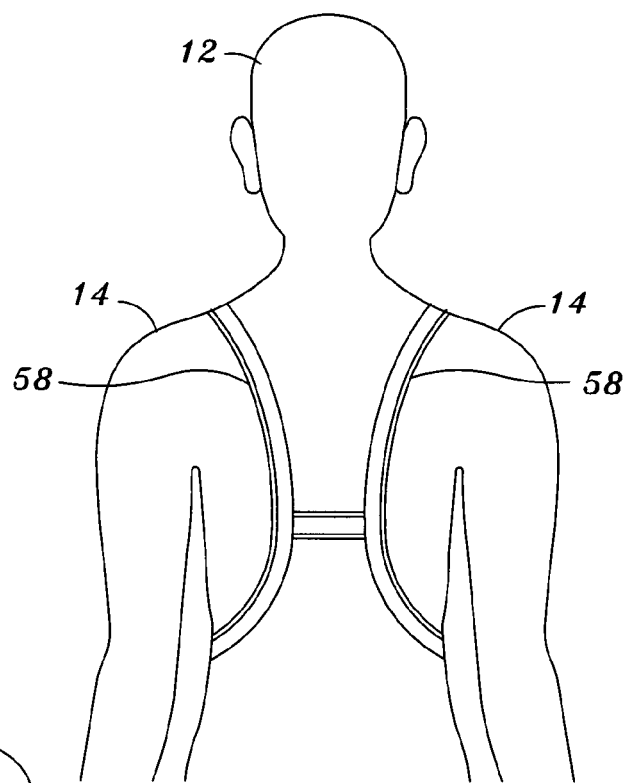
FIG. 9 is a back view of the frontpack assembly secured to the patient by a pair of shoulder straps connected to one another by a cross strap.

The frontpack assembly 56 is preferably secured to the patient's torso by the pair of shoulder straps 58 extending from the upper edge 50 on opposite sides thereof. As was earlier mentioned, the shoulder straps 58 preferably pass over each of the patient's shoulders 14 and wrap underneath the patient's arms 24 along the rib cage and reattaching at the mid portion along the outer edges 48 of the frontpack assembly 56. Alternative strap arrangements are contemplated. For example, as shown in FIG. 9, a cross strap 60 may be provided to interconnect the shoulder straps 58 at a location on the patient's back 22. Adjustable mechanisms may be include in each of the shoulder straps 58 such that the length may be adjusted to fit torsos of different size and shape.

In one embodiment, the motor blower unit 108 may be mounted in a bedside or tabletop housing 104 which is disposed remotely from the frontpack assembly 56 and which is fluidly connected thereto by the extension hose 106 arranged in a manner similar to that which is described above with reference to the vest assembly 32 shown in FIG. 5. The motor blower unit 108 may include the motor assembly 124 configured as a brushless D.C. motor assembly 124 similar to that mentioned above.

Figure 10:
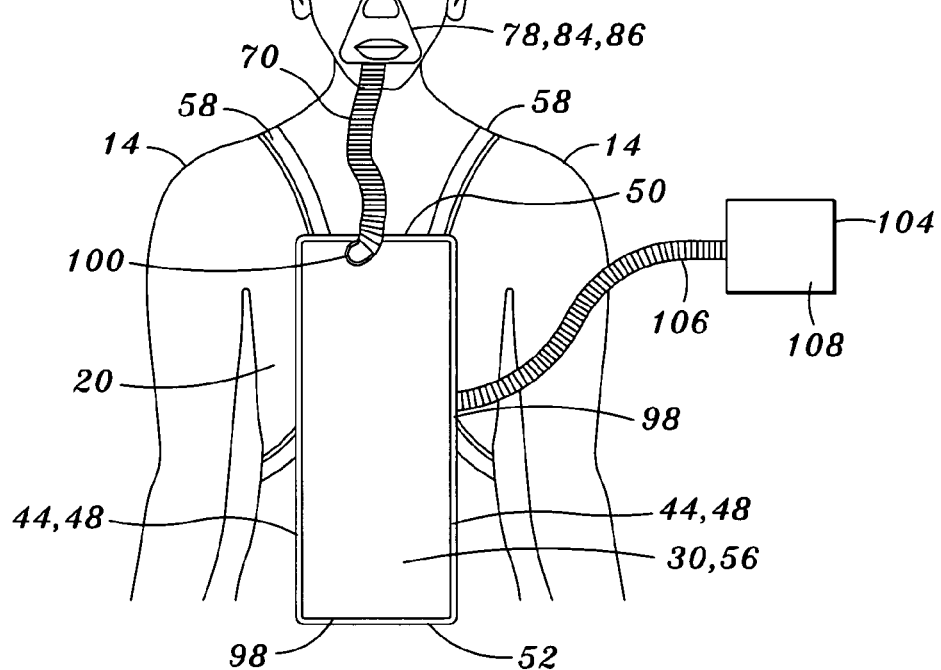
FIG. 10 is a front view of the patient wearing the frontpack assembly and further illustrating the motor blower unit remotely disposed from the frontpack assembly and fluidly connected thereto by means of the extension hose.

Like the vest assembly 32, the frontpack assembly 56 may be optionally configured to allow the user to alternate between the self-contained version and the tabletop version shown in FIG. 10 which is similar to that described above with reference to FIG. 5. The patient hose 70 used in the frontpack assembly 56 may be configured in the various embodiments described for the vest assembly 32 shown in FIGS. 1-6. For example, the patient hose 70 may include ball joints 72 at upper and lower ends thereof in order to allow swivelable connection to the air outlet 100 of frontpack assembly 56 and to the user interface 78.

Figure 11:
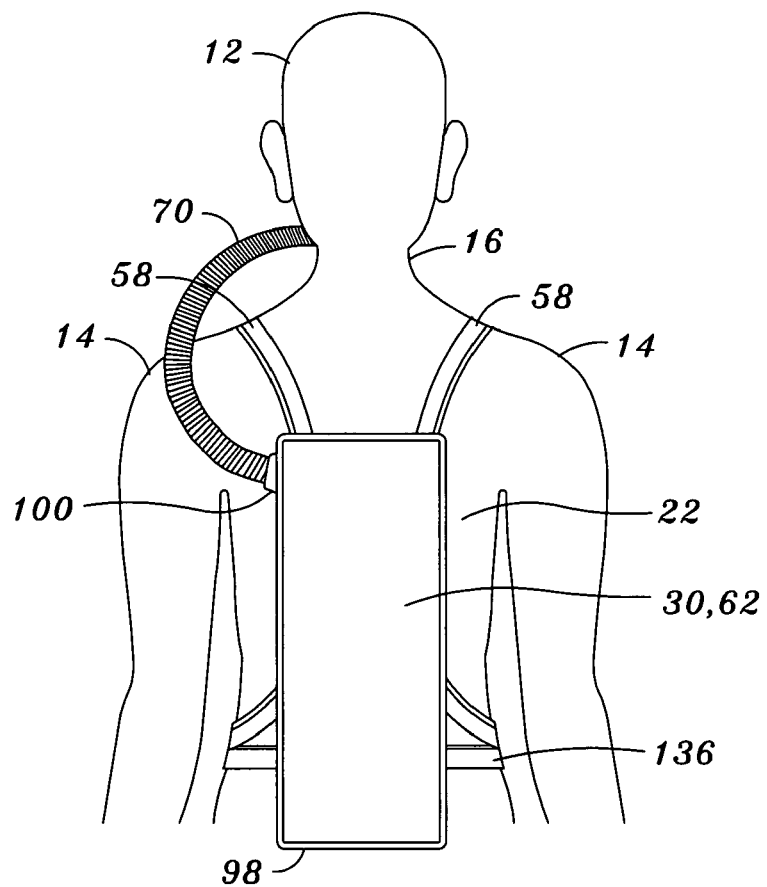
FIG. 11 is a back view of a backpack assembly as worn by the patient.

Shown in FIG. 11 is a portable housing assembly 30 configured in a backpack assembly 62 which is similar in arrangement and function to the frontpack assembly 56 illustrated in FIG. 10 with the exception that the patient hose 70 extends over one of the patient's shoulders 14 to the user interface. The backpack assembly 62 may include a system of straps similar to the shoulder straps 58 of the frontpack assembly 56. More specifically, the shoulder straps 58 may extend from the upper edge 50 of the backpack assembly 62 over the patient's shoulders 14 and underneath the patient's arms 24 along the patient's ribcage before reattaching to the side edges of the backpack assembly 62. An additional waist strap 136 may optionally be included with the frontpack and backpack assemblies 56, 62 in order to secure the lower edge 52 of the backpack assembly 62 to the patient's back 22 as may be desirable when the patient 12 is walking or performing daily activities.

The shoulder straps 58 illustrated in FIG. 11 preferably include length adjustability to allow fitment to a wide range of patients. The backpack assembly 62 may further include a cross strap 60 similar to that which is illustrated in FIG. 9 but which is located adjacent to the patient's chest 20 and which interconnects the shoulder straps 58. The backpack assembly 62 may also be provided in the alternative arrangement illustrated in FIG. 10 wherein the motor blower unit 108 is disposed remotely from the backpack assembly 62 in a tabletop housing 104 and is configured to deliver pressurized gas to the patient 12 by means of the extension hose 106.

The portable housing assembly 30 in any of the above-described arrangements is preferably formed of a resilient material. More specifically, each of the vest assembly 32, frontpack assembly 56 and backpack assembly 62 are preferably filled with a foam material such as open-cell or closed-cell foam or memory foam. The foam is preferably contained with an outer cover formed of a soft material which is comfortably bears against the patient's skin. The resilient material (e.g., foam) preferably includes hollow recesses or cavities 68 formed therein which are sized to receive the operative components (i.e., motor blower unit 108, control unit 130 and power source 132) and which are electrically connected to one another by conductive wiring 134 or by wireless means. By forming the portable housing assembly 30 of resilient material such as foam, the patient 12 may use the CPAP device 10 as a pillow or cushion when sleeping or resting.

Figure 12:
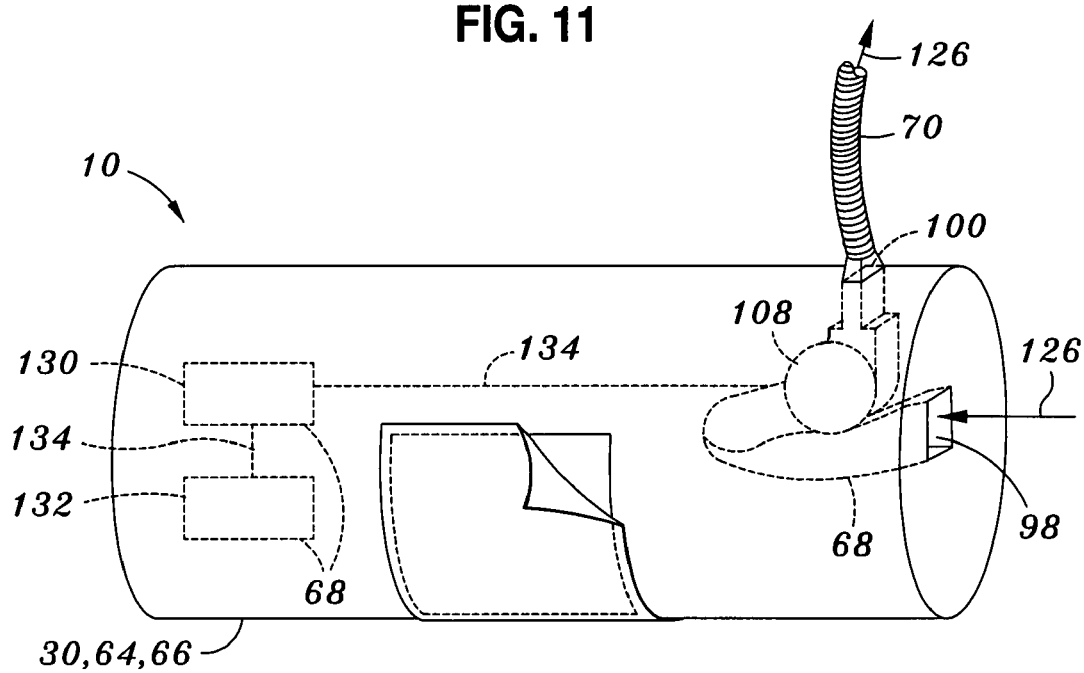
FIG. 12 is a perspective view of the CPAP device wherein the portable housing assembly is configured as a foam-filled pillow assembly having the motor blower unit, control unit and power source contained within cavities formed within the foam.

Referring briefly to FIG. 12, the portable housing assembly 30 may further comprise a pillow assembly 64 or a bedroll assembly 66 configured in a cylindrical shape or other suitable shape and which is adapted for housing the operational components. The pillow or bedroll assembly 64, 66 may be formed of resilient material such as foam and which may be formed of several pieces. For example, the foam may be divided into two halves or sections each having hollow recesses or cavities 68 for housing the motor blower unit 108 on one end of the pillow assembly 64 and the control unit 130 and power source 132 on the opposing end of the pillow assembly 64. In the pillow assembly 64 or bedroll assembly 66, the two halves are insertable into the outer cover through a flap of material which is peelable away to reveal an opening in the outer cover.

The air outlet 100 is preferably located on an end of the pillow or bedroll assembly 64, 66 with the patient hose 70 connecting to the air outlet 100 preferably located on a side of the pillow or bedroll assembly 64, 66. The patient hose 70 extends to the user interface 78 (i.e., nasal mask 86, nasal prongs 88) in the same manner described above with regard to the vest assembly 32 of FIGS. 1-6 and the frontpack and backpack assemblies 56, 62 of FIGS. 7-10. In another arrangement, the portable housing assembly 30 may be configured as a plush toy containing the same operational components described above. The plush toy may be configured in the shape of a stuffed animal or other interesting characters or shapes.

The operation of the CPAP device 10 will now be described with reference to the figures. For self-contained versions, the CPAP device 10 may be assembled by installing the motor blower unit 108, control unit 130 and power source 132 within the portable housing assembly 30 whether configured in a vest assembly 32, frontpack assembly 56, backpack assembly 62, pillow assembly 64 or bedroll assembly 66. As was earlier mentioned, the portable housing assembly 30 is preferably formed of resilient material such as foam having hollow cavities 68 sized and configured to contain the operational components. The vest assembly 32 is mounted on the patient 12 by inserting the patient's head through an opening between the first and second panels 34, 36 such that the collar portion 38 wraps around the nape 18 of the neck 16.

In the frontpack and backpack assemblies 56, 62 illustrated in FIGS. 7-11, the patient's arms 24 are extended through the shoulder straps 58 and the optional cross strap 60 is connected therebetween in order to further stabilize the frontpack assembly 56 and backpack assembly 62 on the patient's chest 20 or back 22. Once the portable housing assembly 30 is mounted on the patient 12, the patient hose 70 may be extended up to the user interface 78 which is then engaged against the patient's airway such as to the patient's nose and/or mouth. The motor blower unit 108 is activated such that compressed air is drawn into the air inlet 98 traveling along the flow path 126 and enters the blower assembly where it is compressed by the impeller 120 before being discharged at the blower outlet 118 (i.e., air outlet 100).

Pressurized air is delivered through the patient hose 70 to the user interface 78 and applied to the patient's airway. The flow characteristics of the pressurized gas (i.e., flow rate, airway pressure) may be adjusted by the patient 12 using the control unit 130. The motor blower unit 108 may be remotely disposed from the portable housing assembly 30 to provide pressurized gas to the user interface 78 via the extension hose 106 as illustrated in FIGS. 5 and 10.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A portable continuous positive airway pressure (CPAP) device adapted for delivering gas under pressure to a patient, the CPAP device comprising:
   a portable housing assembly;
   a motor blower unit disposable within the portable housing assembly and being configured to produce pressurized gas;
   a user interface configured to be engaged to the patient; and
   a patient hose extending between the user interface and the motor blower unit wherein the portable housing assembly comprises a wearable frontpack assembly configured to be worn against the patients chest, and
   wherein the motor blower unit is mounted in a table-top housing and being disposed remotely from the frontpack assembly and fluidly connected thereto by an extension hose.

2. The CPAP device of claim 1 wherein the frontpack assembly includes a pair of shoulder straps disposed on opposing sides thereof.

3. The CPAP device of claim 1 wherein the portable housing assembly comprises a wearable backpack assembly configured to be worn against the patient's back having a pair of shoulder straps disposed on opposing sides thereof.

4. The CPAP device of claim 1 wherein the portable housing assembly comprises a pillow assembly.

5. The CPAP device of claim 1 wherein the portable housing assembly comprises a bedroll assembly.

6. The CPAP device of claim 1 further including a battery pack disposed within the portable housing assembly and being operative to power the motor blower unit.

7. The CPAP device of claim 1 wherein the user interface includes a gas delivery member configured as one of a nasal mask and a pair of nasal prongs.

8. The CPAP device of claim 1 wherein the portable housing assembly is filled with resilient material and having at least one cavity formed therein for containing the motor blower unit.

9. The CPAP device of claim 8 wherein the resilient material is foam.

10. The CPAP device of claim 1 wherein the motor blower unit is configured as a brushless D.C. motor assembly.

11. A portable continuous positive airway pressure (CPAP) device adapted for delivering gas under pressure to a patient, the CPAP device comprising:
    a portable housing assembly;
    a motor blower unit remotely disposable from the portable housing assembly and being configured to produce pressurized gas;
    a user interface configured to be engaged to the patient's airway;
    a patient hose extendable between the user interface and the portable housing assembly; and
    an extension hose extendable between the motor blower unit and the portable housing assembly for delivering pressurized gas to the patient hose.

12. The CPAP device of claim 11 wherein the motor blower unit is mounted in a table-top housing.

13. The CPAP device of claim 11 wherein the portable housing assembly comprises a wearable frontpack assembly configured to be worn against the patient's chest.

14. The CPAP device of claim 13 wherein:
    the patient hose extending from an upper edge of the frontpack assembly to the user interface;
    the extension hose extending from an outer side of the frontpack assembly to the motor blower unit;
    the frontpack assembly fluidly connecting the extension hose to the patient hose.

15. The CPAP device of claim 14 wherein the frontpack assembly includes a pair of shoulder straps disposed on opposing sides thereof.

16. The CPAP device of claim 13 wherein the frontpack assembly further includes a cross strap interconnecting the shoulder straps.

17. The CPAP device of claim 11 wherein the portable housing assembly comprises a wearable backpack assembly adapted to be worn against the patient's back.

18. The CPAP device of claim 11 wherein the user interface includes a gas delivery member configured as one of a nasal mask and a pair of nasal prongs.

* * * * *